United States Patent [19]

Fazio

[11] 4,326,067
[45] Apr. 20, 1982

[54] PROCESS FOR MAKING N-(2-AMINOETHYL)AMIDES

[75] Inventor: Michael J. Fazio, Midland, Mich.

[73] Assignee: The Dow Chemical Company, Midland, Mich.

[21] Appl. No.: 212,476

[22] Filed: Dec. 3, 1980

[51] Int. Cl.³ .................. C07C 85/20; C07C 102/00; C07C 245/18; C07D 205/04; C07D 207/06; C07D 211/14; C07D 223/04; C07D 233/04
[52] U.S. Cl. .................. 548/347; 260/326.43; 260/239 A; 260/239 B; 260/404.5; 525/540; 528/335; 528/423; 544/168; 544/400; 546/233; 546/247; 548/353; 548/355; 564/1; 564/166; 564/182; 564/183; 564/201; 564/224; 564/359; 564/377; 564/386; 564/414; 564/452; 564/453; 564/454; 564/455; 564/457; 564/461; 564/462; 564/488
[58] Field of Search ............... 564/224, 183, 182, 166, 564/201, 488, 454, 455, 461, 462, 1, 414, 359, 377, 386; 260/239 A, 239 B, 404.5 R; 544/168, 400; 546/233, 247

[56] References Cited

U.S. PATENT DOCUMENTS

| | | | |
|---|---|---|---|
| 2,416,552 | 2/1947 | Valko | 564/224 X |
| 4,014,880 | 3/1977 | Dowd et al. | 260/251 R |
| 4,086,273 | 4/1978 | Beranasky et al. | 260/561 S |
| 4,086,274 | 4/1978 | Kaiser et al. | 564/224 X |
| 4,251,459 | 2/1981 | Bargeron et al. | 564/224 X |

OTHER PUBLICATIONS

Seeliger et al., "Angew. Chem. Internat. Edit.", vol. 5, No. 10, pp. 875–888 (1966).
Kormendy, Chem. Abstracts 38:12805f Chem. Abstracts, vol. 58:1445 (1963).
Rosnati, Tetrahedron IX, pp. 175–182 (1960).
Fry, J. Org. Chem. 15, 802 (1950).
Oxazolines, their Preparations, Reactions and Applications, Chem. Reviews, 71, Oct. 1971, pp. 483–506, John Frump.
Dow Sales Brochure: 2-Ethyl-2-Oxazoline XAS–1454.

*Primary Examiner*—John Doll
*Attorney, Agent, or Firm*—Charles J. Enright

[57] ABSTRACT

The process of the invention for preparing a N-(2-substituted aminoethyl)amide of the formula:

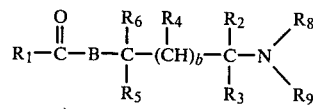

comprises contacting one or more compounds of the formula:

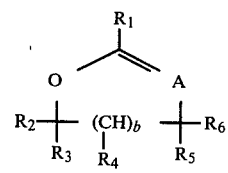

with an amine of the formula:

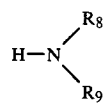

wherein A is nitrogen or a quaternary nitrogen of the formula:

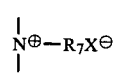

wherein B is

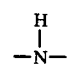

when A is nitrogen and B is

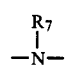

when A is IV;
wherein
  $X^\ominus$ is a counterion;
  b is zero or one; and
  $R_1$–$R_9$ are as defined in the specification.
In a preferred embodiment, the process is catalyzed by a Lewis acid or a protonic acid with a non-nucleophilic counterion.

21 Claims, No Drawings

4,326,067

PROCESS FOR MAKING N-(2-AMINOETHYL)AMIDES

BACKGROUND OF THE INVENTION

This invention relates to a process for making N-(2-aminoethyl)amides or diamines from a 2-oxazoline or 2-oxazine, or a 2-oxazolinium or oxazinium and an amine.

DESCRIPTION OF THE PRIOR ART

In a sales brochure of The Dow Chemical Company, the formation of N-(2-substituted ethyl)amides are described. For example:

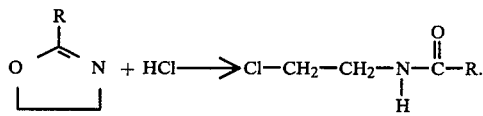

Other substituents such as

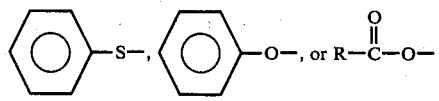

can be substituted for the Cl—.

In *Angew. Chemische* (International Edition) V, No. 10, pp. 875–888 (1966), Seeliger et al. describes the reaction of oxazolines and anilines wherein:

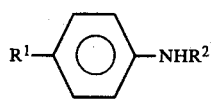

is substituted for HCl in the above reaction.

In *Chemical Abstracts*, 38:12805f, Kormendy et al. disclose the reaction of:

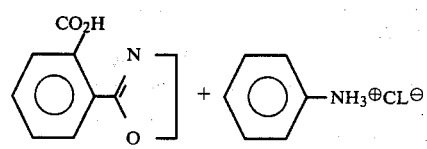

to yield

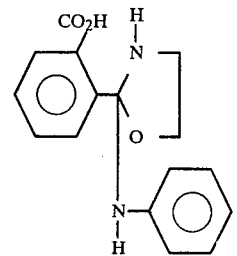

In *Chemical Reviews*, LXXI, No. 5 (1971), pp. 483–505 at page 486, Frump states that when N-(2-bromoethyl)benzamide and diethylamine are boiled together in benzene, 2-phenyl-2-oxazoline is formed.

Rosnati et al. in *Tetrahedron*, IX, pp. 175–82 (1960) reacted ammonia and dimethylamine with a substituted 2-oxazoline to form benzamides.

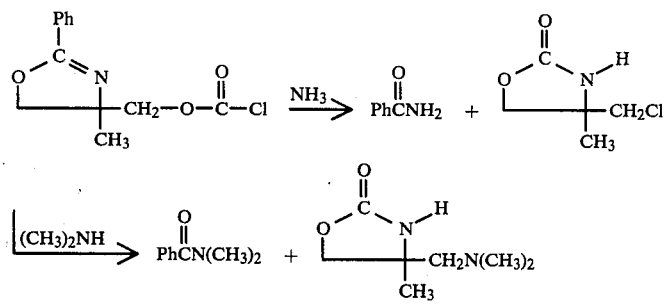

U.S. Pat. No. 4,014,880 discloses the reaction of an oxazoline with ethylene diamine to form 2-ethyl-2-imidazoline and ethanolamine.

U.S. Pat. No. 4,086,274 discloses a process for preparing N-(2-mercaptoethyl)alkanamide by reaction of a 2-oxazoline and hydrogen sulfide. U.S. Pat. No. 4,086,273 discloses a process for preparing $\beta$-aminoethyl sulfides from aliphatic mercaptans and 2-oxazoline.

SUMMARY OF THE INVENTION

The process of the invention for preparing a N-(2-substituted aminoethyl)amide of the formula:

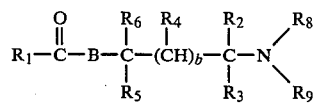

comprises contacting one or more compounds of the formula:

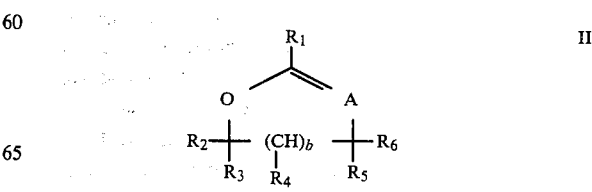

with an amine of the formula:

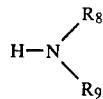 III wherein A is nitrogen or a quaternary nitrogen of the formula:

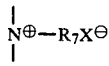 IV wherein B is

when A is nitrogen and B is

when A is IV;
wherein
  $X^{\ominus}$ is a counterion;
  b is zero or one; and
  $R_1$–$R_9$ are as defined below.

In a preferred embodiment, the process is catalyzed by a catalytic amount of a catalyst sufficient to catalyze the reaction; said catalyst being a Lewis acid or a protonic acid with said protonic acid having a non-nucleophilic counterion.

DETAILED DESCRIPTION OF SPECIFIC EMBODIMENTS

The oxazolines and oxazines used in the process of the invention have the structure:

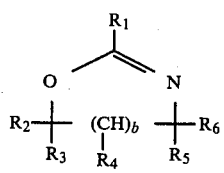 IIa wherein b is zero for the oxazolines and one for the oxazines. Oxazolines are preferred.

The 2-oxazolines and 2-oxazines of the process of the invention are generally known compounds. Methods for their synthesis are discussed in Frump and Seeliger et al., supra. Specific methods for making the oxazolines are disclosed in U.S. Pat. No. 4,203,900. These three references are hereby incorporated by reference.

$R_1$ is hydrogen or an aliphatic or aromatic radical or an inertly-substituted aliphatic or aromatic radical having generally up to 25 carbon atoms. $R_1$ can be a link in a polymer backbone. For example in the structure:

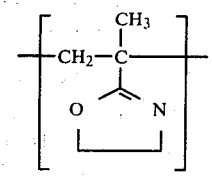

which can be a homopolymer or heteropolymers as described in U.S. Pat. No. 3,505,297 which is hereby incorporated by reference. Comonomers are limited to those with functionality that does not react with the amine, e.g., styrene, vinylpyridine, ethylene, etc.

$R_1$ may also represent a link to a second oxazoline ring to form a bis-oxazoline as exemplified by the structure:

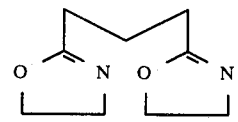

which is disclosed in U.S. Pat. Nos. 2,569,428 and 3,419,520 which are hereby incorporated by reference.

A key aspect is that $R_1$ is inert when it is exposed to other reactants under the reaction conditions. By inert it is meant that $R_1$ will not react with amines, will not sterically hinder the ring opening reaction, and will not react at a rate faster nor at a rate significantly close to that of the amines with other substituents in its own or other similar molecules. For example, $R_1$ can be hydrogen, methyl, ethyl, undecyl, stearyl, phenyl, benzyl, hydroxyethyl, or p-nitrophenyl. Inert substituents include, for example, the radicals capable of being $R_1$, ethers, thioethers, amides, hydroxy and tertiary amines. $R_1$ is preferably a straight chain aliphatic radical of 1–12 carbon atoms. $R_1$ is most preferably ethyl. $R_2$–$R_6$ which may be the same or different, have the same definition as $R_1$ except that the most preferred embodiment is hydrogen. $R_4$, of course, does not exist in the oxazoline structure.

Where A is

 IV the starting compounds are oxazoliniums or oxaziniums where b is zero for oxazoliniums and one for oxaziniums. $R_1$–$R_6$ have the same definition and preferred embodiments as the oxazolines and oxazines.

The primary difference between the oxazoline/-oxazine structures and the oxazolinium/oxazinium structures is that the latter have a quaternized nitrogen with the accompanying radical $R_7$ and the counterion $X^{\ominus}$. Upon reaction, the counterion reacts with a hydrogen made available by the reaction to form HX.

$R_7$ has the same definition as $R_2$ with methyl being most preferred. The oxazoliniums and oxaziniums of this invention are prepared by adding an alkylating agent to the oxazoline or oxazine. This reaction and these salts are discussed in Frump, Supra at page 497 which is hereby incorporated by reference. Representative alkylating agents are: methyl tosylate, benzyl chloride, and methyl iodide.

The counterion $X^{\ominus}$ is one which will not react with the oxazolines or oxazines under the reaction conditions used.

The amines used in the process of the invention have the structure:

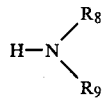
III $R_8$ and $R_9$, which can be the same or different are hydrogen, an aliphatic or cycloaliphatic or an inertly-substituted aliphatic or cycloaliphatic radical; $R_{10}NH_2$ wherein $R_{10}$ is an aliphatic or cycloaliphatic chain or inertly-substituted aliphatic or cycloaliphatic chain of from 4 to 25 carbon atoms which separate the two nitrogen atoms by at least 4 carbon atoms; or $R_8$, $R_9$ and the mediate nitrogen atom together form an aliphatic or an inertly-substituted aliphatic heterocyclic ring containing four to seven members and preferably five or six members.

Representative examples of $R_8$ and $R_9$ are methyl, ethyl, n-propyl, n-butyl, iso-propyl, 2-methyl butyl, 2-phenyl propyl, cyclohexyl, etc. Methyl and ethyl are preferred. Representative examples of a ring formed by $R_8$, $R_9$ and the mediate nitrogen atom are: N-pyrrolidinyl, 2-methyl-N-pyrrolidinyl, N-piperidinyl, N-piperazinyl, N-morpholinyl, etc.

$R_{10}NH_2$ can be 4-amino n-butyl, 5-amino, 4-methyl-n-pentyl, etc. The substituents on $R_8$, $R_9$, the rings formed by $R_8$ and $R_9$ and on $R_{10}$ may be inertly-substituted. By inert it is meant that the substituent group is substantially less nucleophilic than the nitrogen mediate $R_8$ and $R_9$ of III. That is, the substituent reacts with oxazolines not at all or at most at a substantially slower rate than the above cited nitrogen. Examples of inert substituents include: hydroxyl, ethers, aliphatic or aromatic hydrocarbon radicals, esters, tertiary amines, amides and the groups which can be $R_8$ or $R_9$.

$R_8$ and/or $R_9$ can also be a polymeric backbone. Examples include the polyamines such as triethylamine tetraamine.

In a preferred process of the invention, the reaction is catalyzed by a catalytic amount of a Lewis acid or a protonic acid wherein the protonic acid has a non-nucleophilic counterion. By a catalytic amount is meant an amount substantially less than molar equivalency. A catalytic amount is generally less than 5 mole percent based on the oxazoline. Preferably, the catalyst is present at from about 0.01 mole percent to about 2 mole percent based on the oxazoline.

Lewis acids are well-known to those skilled in the art and are generally defined as a substance that can take up an electron pair to form a covalent bond. Representative examples include $BF_3$, $AlCl_3$, $SnCl_4$, $ZnCl_2$, $FeCl_2$, $H_2WO_3$, $Fe_2SO_4$, $Zn(O_2CCH_3)_2$, $CdCl_2$, $CoCl_2$, and $I_2$. Protonic acids with non-nucleophilic counterions or anions are also a known class of compounds. Protonic acids contain hydrogen. Representative examples include: p-toluenesulfonic acid, sulfuric acid and phosphoric acid. The preferred catalysts are Lewis acids. The most preferred is zinc acetate.

The amino amides formed have the structure:

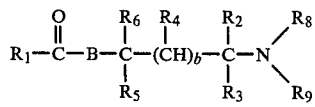
I wherein $R_1$-$R_{10}$ have the definitions cited above and B is

when A is nitrogen and B is

when A is IV. When oxazolines are reacted, B is

b is zero, and $R_4$ and $R_7$ will not be part of the product.

A preferred reaction is that of 2-ethyl-2-oxazoline with either diethyl- or dimethylamine. The product formed is N-(2-diethylaminoethyl)propionamide or N-(2-dimethylaminoethyl)propionamide, respectively.

The process of the invention may be used to form polymers. For example, the combination of:

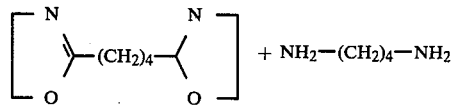

yields alternating monomer units of the structures:

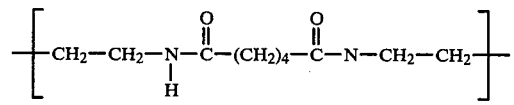

and

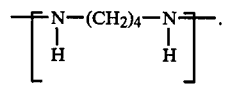

The process of the invention may also be used as a cross-linking reaction. For example, with polymers with pendant oxazolines of the structure:

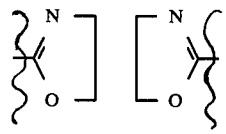

addition of a diamine of the invention such as

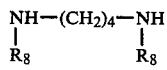

yields:

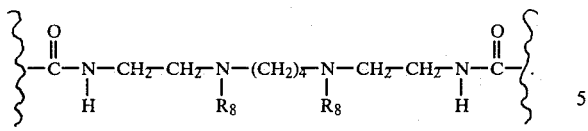

Conversely, bis-oxazolines will cross-link polymers with pendant amine groups.

The process of the invention is carried out at a temperature high enough to permit reaction. The reactants are normally in the liquid state. Preferably, the reaction is carried out at a minimum temperature of about 50° C. More preferably, it is carried out at a minimum of about 100° C.

The maximum temperature feasible is that at which the reactants thermally decompose or form significant quantities of by-products. Normally the maximum desirable temperature is no more than about 250° C. Preferably, the temperature is at or below about 225° C. Most preferably, the reaction is carried out at a temperature from about 100° C. to about 225° C.

The process of the reaction is normally and preferably carried out at autogenous pressure. That is, at atmospheric pressure or, if it is higher, the vapor pressure of the combined reactants at the reaction temperature. However, lower or higher pressures are feasible.

The reaction may be carried out in a solvent inert to the reactants but is preferably done neat. Suitable solvents include toluene, ethers and p-dichlorobenzene.

The reactants are generally added in equimolar amounts, although an excess, for example, of a cheaper reactant can be used. Preferably, the reactants will have an oxazoline/amine ratio of from about 0.9 to about 1.1.

Further reactions of the products of the process of the invention are also of interest. These reactions when combined with the inventive process are also considered inventive and within the scope of the invention. The N-(2-aminoethyl)amides can undergo hydrolysis to diamines and carboxylic acids. For example:

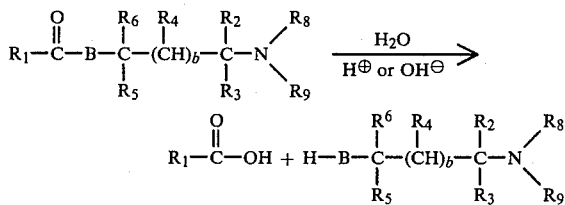

In the case of the reaction of 2-ethyl-2-oxazoline with dimethylamine, the hydrolysis of the amide yields propanoic acid and N,N-dimethylethylenediamine. The hydrolysis of an amide to an amine is well-known and is discussed in U.S. Pat. Nos. 3,592,854 and 3,457,311 which are hereby incorporated by reference. Fifteen percent aqueous caustic (NaOH or KOH) is the preferred hydrolysis medium.

The amide products of the inventive process also undergo transamidation. That is, the amide is contacted with, for example, a high boiling amine which changes places with the amine functionality of the amide. For example:

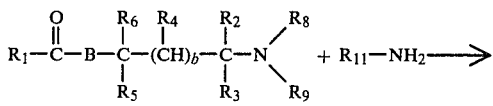

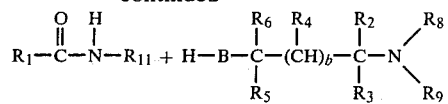

In a preferred embodiment the reaction is:

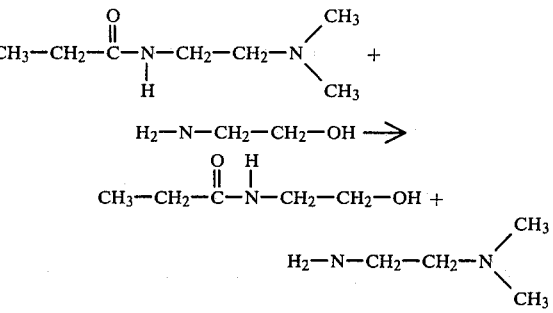

The N-(2-hydroxyethyl)propionamide by-product may then be reacted to form more 2-ethyl-2-oxazoline. When $R_8$=H and B=

the amino amide formed may also undergo a cyclization to form an imidazoline. For example:

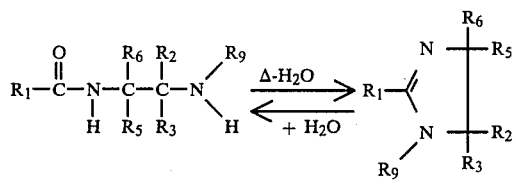

The imidazolines may be hydrolyzed to again form the N-(2-aminoethyl)amide.

The compounds formed by the process of the invention are generally known and have many uses. N-(2-dialkylaminoethyl)alkylamides are taught to retard the ripening of fruit in U.S. Pat. No. 4,148,926. The N,N-dialkylethylenediamines are known to be useful as: a stabilizer for polystyrene (U.S. Pat. No. 2,873,264); in leather dyeing (CA 66:76949z); dye acceptors for acrylic and vinyl copolymers (CA 51:15176b); curing agents for polyepoxides (U.S. Pat. No. 4,201,854); and as intermediates for many other compounds such as procaineamide.

EXAMPLE 1

A 90-ml stainless steel reactor is charged with 28.18 gm (0.285 mole) of 2-ethyl-2-oxazoline, 20.7 gm (0.284 mole) of diethylamine and 0.54 gm (0.003 mole) of zinc acetate. The reactor is purged with nitrogen, sealed and heated to 225° C. After 19 hours, at that temperature and at autogenous pressure, the reactor is cooled to room temperature and the contents of the reactor analyzed. 5.56 Weight percent diethylamine, 1.03 weight percent ethyloxazoline and 81.4 weight percent N-(2-diethylaminoethyl)propionamide are found.

EXAMPLE 2

Phenyl-2-oxazoline (37 mmoles), diethylamine (37 mmoles) and zinc acetate (0.6 mmole) is charged to a 45-ml Parr reactor and heated to 170° C.–175° C. for 20 hours at autogenous pressure. Analysis shows 11.9 weight percent unreacted amine, 7.3 weight percent unreacted phenyloxazoline and 57.5 weight percent N-(2-diethylaminoethyl)benzamide.

EXAMPLE 3

Undecyloxazoline (53 mmoles), diethylamine (104 mmoles) and 0.9 mmole of zinc acetate are reacted under conditions similar to Example 2 to yield 87 percent of theoretical N-(2-diethylaminoethyl)undecylamide.

EXAMPLES 4–12

Different catalysts are compared at approximately one mole percent concentrations with reactants and conditions similar to Example 1. Table A gives results as a weight percent of theoretical yield based on the oxazoline.

TABLE A

| Example | Catalyst | % Yield |
|---|---|---|
| 4 | No Catalyst | 7.8 |
| 5 | $H_2WO_3$ | 62.5 |
| 6 | $Fe_2 SO_4 nH_2O$ | 79.4 |
| 7 | $Zn(CH_3COO)_2 \cdot 2.5H_2O$ | 82.5 |
| 8 | $Zn(CH_3COO)_2$ | 84.4 |
| 9 | $CdCl_2 \cdot 2H_2O$ | 80.2 |
| 10 | $BF_3 \cdot$ diethylether | 88.5 |
| 11 | $CoCl_2$ | 86.0 |
| 12 | p-toluene sulfonic acid | 86.0 |

EXAMPLE 13

5.2 Gm (23 mmoles) of dibutylamine and 2.5 gm (25 mmoles) of ethyloxazoline are reacted in a stainless steel tube with 52 mg (0.3 mmole) of zinc acetate at 205° C. at autogenous pressure for 24 hours. Yield determined by analysis of the crude product is 85 percent N-(2-dibutylaminoethyl)propionamide.

EXAMPLE 14

Under the same conditions as Example 13, 2.5 gm (25 mmoles) of 2-ethyl-2-oxazoline, 1.84 gm (25 mmoles) of t-butylamine and 49.4 mg (0.27 mmole) of zinc acetate are reacted to yield 64 percent N-(2-t-butylaminoethyl)-propionamide.

EXAMPLE 15

Under the same conditions as Example 13, 2.5 gm (25 mmoles) of 2-ethyl-2-oxazoline, 2.2 gm (25 mmoles) of morpholine and 0.59 mg of zinc acetate are reacted to yield 83 percent N-(2-morpholinylethyl)propionamide.

EXAMPLE 16

28.9 Gm of 2-ethyl-2-oxazoline, 17.4 gm of monoethanolamine and 0.71 gm of zinc acetate are charged to a 90-ml stainless steel reactor. The mixture is heated at autogenous pressure at 200° C. for 20 hours. Analysis shows three major components: N-(N-2-hydroxyethyl-2-aminoethyl)propionamide; 1-(2-hydroxyethyl)-2-ethylimidazoline and N-aminoethyl-N-hydroxyethyl propionamide. Hydrolysis of this mixture yields a mixture of N-(2-hydroxyethyl)ethylenediamine, propionic acid and a small amount of unreacted monoethanolamine.

What is claimed is:

1. A process for preparing a N-(2-substituted aminoethyl)amide of the formula:

$$R_1-\overset{O}{\overset{\|}{C}}-B-\overset{R_6}{\underset{R_5}{\overset{|}{C}}}-\overset{R_4}{\underset{R_3}{\overset{|}{C}}}-(CH)_b-\overset{R_2}{\overset{|}{C}}-N\overset{R_8}{\underset{R_9}{}} \qquad I$$

the process comprising contacting one or more compounds of the formula:

$$\begin{array}{c} R_1 \\ \diagup \diagdown \\ O \quad A \\ R_2 \text{---}(CH)_b \text{---} R_6 \\ R_3 \quad R_4 \quad R_5 \end{array} \qquad II$$

with an amine of the formula:

$$H-N\overset{R_8}{\underset{R_9}{}} \qquad III$$

and wherein A is nitrogen or a quaternary nitrogen of the formula:

$$\overset{|}{\underset{|}{N^{\oplus}}}-R_7X^{\ominus} \qquad IV$$

wherein B is $$\overset{H}{\underset{|}{-N-}}$$

where A is nitrogen and B is $$\overset{R_7}{\underset{|}{-N-}}$$

when A is IV; wherein $X^{\ominus}$ is a counterion; and wherein $R_1$–$R_7$, which may be the same or different, are each hydrogen, an aliphatic or cycloaliphatic or aromatic radical, or an inertly-substituted aliphatic, cycloaliphatic or aromatic radical; and wherein $R_8$ and $R_9$, which are the same or different, are hydrogen, an aliphatic or cycloaliphatic or inertly-substituted aliphatic or cycloaliphatic radical; or $R_8$ and/or $R_9$ are:

$R_{10}NH_2$ wherein $R_{10}$ is an aliphatic or cycloaliphatic or an inertly-substituted aliphatic or cycloaliphatic chain containing from 4 to 25 carbon atoms which separates the 2 nitrogen atoms by at least 4 carbon atoms; or $R_8$, $R_9$ and the mediate nitrogen atom form an inertly-substituted or unsubstituted aliphatic heterocyclic ring containing from 4 to 7 members; and wherein b is zero or 1.

2. The process of claim 1 wherein the process is catalyzed by a catalytic amount of a Lewis acid or a protonic acid, said protonic acid having a non-nucleophilic counterion.

3. The process of claim 2 wherein the catalyst is $H_2WO_3$, $FeSO_4$, $Zn(CH_3COO)_2$, $CdCl_2$, $BF_3$, $CoCl_2$, sulfuric acid, phosphoric acid or p-toluene sulfonic acid.

4. The process of claim 2 wherein the catalyst is present in an amount of less than about 5 mole percent.

5. The process of claim 4 wherein the catalyst is present in an amount of from about 0.01 mole percent to about 2 mole percent.

6. The process of claim 2 wherein A is nitrogen and b is zero.

7. The process of claim 6 wherein $R_2$, $R_3$ and $R_5$, which may be the same or different are hydrogen or aliphatic hydrocarbyl radicals containing 1–12 carbon atoms.

8. The process of claim 7 wherein $R_2$, $R_3$ and $R_5$ are hydrogen.

9. The process of claim 6 wherein $R_1$ is phenyl or an aliphatic hydrocarbyl radical containing from 1–12 carbon atoms.

10. The process of claim 9 wherein $R_1$ is ethyl.

11. The process of claim 1 wherein II is 2-ethyl-2-oxazoline.

12. The process of claim 6 wherein $R_8$ and $R_9$, which may be the same or different, are aliphatic hydrocarbyl radicals containing from 1–12 carbon atoms.

13. The process of claim 12 wherein $R_8$ and $R_9$ are the same and are methyl or ethyl.

14. The process of claim 6 wherein $R_8$, $R_9$ and the mediate nitrogen atom form an aliphatic heterocyclic ring having 4 to 7 members.

15. The process of claim 14 wherein III is hydrocarbyl substituted or unsubstituted, morpholine, pyrrolidine, piperidine, or piperazine.

16. The process of claim 6 wherein the contacting is carried out at a temperature of from about 50° C. to about 250° C.

17. The process of claim 16 wherein the temperature is from about 100° C. to about 225° C.

18. The process of claim 6 wherein the contacting is carried out at autogenous pressure.

19. The process of claim 6 including the additional steps of:
(a) hydrolyzing I to form an amine and a carboxylic acid; and
(b) recovering said amine.

20. The process of claim 6 wherein $R_9$ is hydrogen including the additional steps of:
(a) heating to dehydrate I and form an imidazoline of the structure

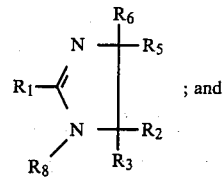

; and (b) recovering said imidazoline.

21. A process comprising the steps of contacting 2-ethyl-2-oxazoline with dimethylamine, diethylamine or pyrrolidine in the presence of a catalytic amount of a catalyst comprising a Lewis acid or a protonic acid with a non-nucleophilic counterion, to form N-(2-dimethylaminoethyl)propionamide, N-(2-diethylaminoethyl)propionamide, or N-(2-pyrrolidinylethyl)propionamide, respectively.

* * * * *

UNITED STATES PATENT AND TRADEMARK OFFICE
CERTIFICATE OF CORRECTION

PATENT NO. : 4,326,067

DATED : April 20, 1982

INVENTOR(S) : Michael J. Fazio

It is certified that error appears in the above—identified patent and that said Letters Patent is hereby corrected as shown below:

Column 1, line 65, the end of the formula, delete "$\langle\bigcirc\rangle-NH_3^{\oplus}CL^{\ominus}$" and insert therefor -- $\langle\bigcirc\rangle-NH_3^{\oplus}Cl^{\ominus}$ --.

Column 5, line 46, delete "triethylamine" and insert -- triethylene --.

Column 7, line 46, second formula, delete "$R^6$" and insert therefor -- $R_6$ --.

Column 10, line 45, delete "where" and insert -- when --.

Signed and Sealed this

Seventeenth Day of August 1982

[SEAL]

Attest:

GERALD J. MOSSINGHOFF

Attesting Officer

Commissioner of Patents and Trademarks